United States Patent
Simanzhenkov et al.

(10) Patent No.: US 11,691,130 B2
(45) Date of Patent: *Jul. 4, 2023

(54) CATALYST FOR ETHANE ODH

(71) Applicant: NOVA Chemicals (International) S.A., Fribourg (CH)

(72) Inventors: Vasily Simanzhenkov, Calgary (CA); Xiaoliang Gao, Calgary (CA); David Jeffrey Sullivan, Calgary (CA); Leonid Modestovich Kustov, Moscow (RU); Aleksey Victorovich Kucherov, Moscow (RU); Elena Dmitrievna Finashina, Moscow (RU)

(73) Assignee: NOVA Chemicals (International) S.A.

(*) Notice: Subject to any disclaimer, the term of this patent is extended or adjusted under 35 U.S.C. 154(b) by 635 days.

This patent is subject to a terminal disclaimer.

(21) Appl. No.: 16/747,131

(22) Filed: Jan. 20, 2020

(65) Prior Publication Data

US 2020/0171469 A1 Jun. 4, 2020

Related U.S. Application Data

(63) Continuation of application No. 15/617,426, filed on Jun. 8, 2017, now Pat. No. 10,576,461.

(30) Foreign Application Priority Data

Jun. 20, 2016 (CA) ..................... 2933484

(51) Int. Cl.
| | | |
|---|---|---|
| *B01J 27/057* | (2006.01) | |
| *B01J 23/00* | (2006.01) | |
| *C07C 5/48* | (2006.01) | |
| *B01J 37/10* | (2006.01) | |
| *B01J 37/02* | (2006.01) | |
| *B01J 23/652* | (2006.01) | |
| *B01J 37/04* | (2006.01) | |
| *B01J 37/08* | (2006.01) | |

(52) U.S. Cl.
CPC ......... *B01J 27/0576* (2013.01); *B01J 23/002* (2013.01); *B01J 23/6525* (2013.01); *B01J 37/0207* (2013.01); *B01J 37/0213* (2013.01); *B01J 37/0236* (2013.01); *B01J 37/04* (2013.01); *B01J 37/08* (2013.01); *B01J 37/10* (2013.01); *C07C 5/48* (2013.01); *B01J 2523/00* (2013.01); *Y02P 20/52* (2015.11)

(58) Field of Classification Search
None
See application file for complete search history.

(56) References Cited

U.S. PATENT DOCUMENTS

| | | |
|---|---|---|
| 4,250,346 A | 2/1981 | Young et al. |
| 4,524,236 A | 6/1985 | McCain |
| 7,718,568 B2 | 5/2010 | Gaffney et al. |
| 8,105,971 B2 | 1/2012 | Gaffney et al. |
| 8,519,210 B2 | 8/2013 | Arnold et al. |
| 9,156,764 B2 | 10/2015 | Han et al. |
| 10,343,957 B2 | 7/2019 | Serhal et al. |
| 10,538,465 B2 | 1/2020 | Serhal et al. |
| 10,576,461 B2 | 3/2020 | Simanzhenkov et al. |
| 10,647,635 B2 | 5/2020 | Simanzhenkov et al. |
| 11,053,179 B2 | 7/2021 | Olayiwola et al. |
| 11,111,194 B2 | 9/2021 | Simanzhenkov et al. |
| 11,306,044 B2 | 4/2022 | Olayiwola et al. |
| 11,447,434 B2 | 9/2022 | Simanzhenkov et al. |
| 2020/0156055 A1 | 5/2020 | Goodarznia et al. |
| 2020/0171468 A1 | 6/2020 | Simanzhenkov et al. |
| 2021/0040018 A1 | 2/2021 | Gent et al. |
| 2022/0251004 A1 | 8/2022 | Simanzhenkov et al. |
| 2022/0380277 A1 | 12/2022 | Simanzhenkov et al. |
| 2022/0396541 A1 | 12/2022 | Simanzhenkov et al. |

FOREIGN PATENT DOCUMENTS

| | | |
|---|---|---|
| EP | 1693107 | 8/2006 |
| EP | 1908518 | 4/2008 |
| JP | H10-17523 | 1/1998 |

OTHER PUBLICATIONS

Kum et al, "Performance of Pd-promoted Mo—V—Te—Nb—O catalysts in the partial oxidation of propane to acrylic acid," Applied Catalysis A: General, 365, pp. 79-87 (Year: 2009).*
Fasi, Andras; Kiss, Janos T.; Torak, Bela and Palinko, Istvan; The selectivity and activity determining roles of carbonaceous species and metal-metal oxide interface in metal-catalyzed hydrogenation and isomerization reactions; Applied Catalysis A: General 200 (2000), pp. 189-200.
PCT International Search Report and Written Opinion in International Appln. PCT/IB2017/053428, dated Oct. 11, 2017, 12 pages.
PCT International Preliminary Report on Patentability in International Appln. PCT/IB2017/053428, dated Dec. 25, 2018, 8 pages.
Watanabe et al., "New Synthesis Route For Mo-V-Nb-Te Mixed Metal Oxides for Propane Ammoxidation," Applied Catalysis A: General, Mar. 13, 2000, 194-195, pp. 479-485.

* cited by examiner

*Primary Examiner* — Colin W. Slifka
(74) *Attorney, Agent, or Firm* — Fish & Richardson P.C.

(57) ABSTRACT

A catalyst for oxidative dehydrogenation (ODH) of ethane with an empirical formula Mo—V—Te—Nb—Pd—O produced using a process comprising impregnation of the Pd component on the surface of the catalyst following a calcination step using a Pd compound free of halogens. The resulting catalyst can be used in both diluted and undiluted ODH processes and shows higher than expected activity without any loss of selectivity.

19 Claims, No Drawings

CATALYST FOR ETHANE ODH

CROSS REFERENCE TO RELATED APPLICATIONS

This application is a continuation application of U.S. application Ser. No. 15/617,426, filed Jun. 8, 2017, which claims the benefit of the earlier filing date of Canadian application serial number 2933484 filed on Jun. 20, 2016. The contents of each are incorporated herein by reference in their entirety.

BACKGROUND

The present disclosure relates to a catalyst for oxidative dehydrogenation (ODH) of ethane comprising the elements molybdenum, vanadium, tellurium, niobium, palladium, and oxygen. The catalyst is produced in a process where incorporation of palladium into the catalyst, using a palladium compound that is free from halogens, is performed after a calcination step. The catalyst is useful for both diluted and undiluted ODH processes and shows higher activity than prior art catalysts without any concurrent loss of selectivity.

Conversion of paraffins (alkanes) to olefins can be achieved in a number of ways. The most widely practiced method is thermal cracking technology, where paraffins are exposed to temperatures as high as 1000° C. for very short time periods, in the order of milliseconds to a few seconds, promoting the loss of hydrogen and subsequent formation of one or more unsaturated bonds characteristic of olefins. However, the current thermal cracking processes are not only cost intensive to build and operate but also energy intensive due to the substantial heat requirement for the endothermic cracking reactions. Also, significant amounts of $CO_2$ are produced from the operation of cracking furnaces.

Alternatively, conversion of paraffins can be accomplished using an oxidative dehydrogenation (ODH) process where a stream of one or more alkanes are passed over an oxidative dehydrogenation catalyst, in the presence of oxygen or an oxygen containing gas, at temperatures from about 300° C. to 750° C. The advantages of catalytic ODH over steam cracking are that it provides higher ethane conversion and higher ethylene selectivity while using lower reaction temperatures. On the downside, the risk of thermal runaway of the reaction and consequential explosion requires extensive safety precautions. Also, developing catalysts is made difficult because olefins are more reactive than the paraffins they are derived from, creating the potential for further oxidation to unwanted byproducts. It is therefore desirable to use catalysts that are more selective for oxidation of paraffins than olefins.

Use of mixed metal oxides as catalysts for ODH is well known. U.S. Pat. No. 4,250,346 issued Feb. 10, 1981 to Young and Thorsteinson, assigned to Union Carbide Corporation, claims a process for converting ethane to ethylene using temperatures below 550° C. The catalyst employed uses mixed metal oxides and is of the formula Mo—X—Y, where X=Cr, Mn, Nb, Ta, Ti, V and/or W and Y=Bi, Ce, Co, Cu, Fe, K, Mg, Ni, P, Pb, Sb, Si, Sn, TI and/or U.

U.S. Pat. No. 4,524,236, issued Jun. 18, 1985 to McCain assigned to Union Carbide Corporation, claims a process for converting ethane to ethylene using an ODH catalyst of the formula Mo—V—Nb—Sb—X, where X=Li, Sc, Na, Be, Mg, Ca, Sr, Ba, Ti, Zr, Hf, Y, Ta, Cr, Fe, Co, Ni, Ce, La, Zn, Cd, Hg, Al, TI, Pb, As, Bi, Te, U, and W. The examples include the process for making the catalyst which includes a calcination step where the catalyst was heated to 350° C. for up to five hours. When used in either the presence or absence of water the catalyst shows a selectivity of 75% for a conversion rate of 50%. Conditions for ODH using this invention included the addition of more than 85% of the inert diluent helium.

U.S. Pat. No. 8,105,971, issued Jan. 31, 2012 to Gaffney et al., assigned to Lummus Technology Inc., claims a process for making a catalyst of the formula Mo—V—X—Y—Z—O, where X=at least one of Nb and Ta, Y=at least one of Sb and Ni, and Z=at least one of Te, Ga, Pd, W, Bi, and Al. The process requires admixing all the components followed by a pH adjustment with nitric acid before drying, calcining, and grinding the final product with acid. Claims include a requirement for selectivity of the catalyst exceeding 90% with an ethane conversion of at least 70% when used in an ODH process where molar ratios of ethane, oxygen, water, and nitrogen used are either 10/10/10/70 or 15/10/10/65. U.S. Pat. No. 8,519,210 issued Aug. 27, 2013 to Arnold et al., assigned to Lummus Technology Inc., provides examples that include the same catalyst and process for making said catalyst.

U.S. Pat. No. 7,718,568, issued May 18, 2010 to Gaffney et al., assigned to Rohm and Haas Company, claims a catalyst useful for conversion of an alkane, or a mixture of an alkane and an alkene, to unsaturated carboxylic acids, or in the presence of ammonia, unsaturated nitrites, of the formula Mo—V—M—Nb—X—O, where M is a group consisting of Te and Sb, and X is selected from the group consisting of Li, Na, K, Rb, Cs, Mg, Ca, Sr, Ba, Sc, Y, La, Ti, Zr, Hf, Ta, Cr, W, Mn, Re, Fe, Ru, Co, Rh, Ir, Ni, Pd, Pt, Cu, Ag, Au, Zn, B, Ga, In, Pb, P, As, Sb, Bi, Se, F, Cl, Br, I, Pr, Nd, Sm and Tb, provided that when M is Sb, X cannot be Sb. The patent also claims a process for making the catalyst, said process including admixing all the components in two steps, separated and followed by hydrothermal treatment. Calcination of the resulting insoluble materials is optional.

DETAILED DESCRIPTION

The present disclosure provides a process for making a highly active and selective mixed metal oxide oxidative dehydrogenation catalyst of the formula Mo—V—Nb—Te—Pd—O produced in a process whereby the Pd component is added after a calcination step. The Mo, V, Nb, and Te components are admixed together and then subjected to hydrothermal treatment followed by calcination, prior to addition of the Pd component. An oxide catalyst prepared with Mo, V, Nb, and Te, the four component catalyst, demonstrates lower activity than a similar catalyst containing, in addition to the same elements, small amounts of Pd impregnated onto its surface. Catalyst produced by direct incorporation of the Pd component during initial admixing of all the components shows lower activity than a catalyst where the Pd component is added after the calcination step. Surprisingly, when the Pd impregnated catalyst is subjected to calcination, as is common for these catalysts, the activity is lower than a catalyst where there is no calcination after the impregnation of Pd. Furthermore, the increase of activity seen with the catalyst disclosed herein is not accompanied by a decrease in selectivity for ethylene, an effect that is dependent upon the nature of the Pd compound used to impregnate the surface of the catalyst with Pd. Specifically, a catalyst produced using a Pd component containing a halogen, $PdCl_2$ for example, while maintaining high selectivity for ethylene, does not demonstrate higher activity compared to the four component catalyst. Last, the added benefit of this catalyst is that it can be used in an ODH process that does not require dilution of the reactants, oxygen and ethane, with any inert gas such as nitrogen or water. As a result, costly downstream processing for removal of excess oxygen, unwanted by products, and water are limited or not required.

Provided is a process of making a mixed metal oxide catalyst of the formula Mo—V—Nb—Te—Pd—O, in the respective relative atomic proportions of a, b, c, d, and e wherein when a=1, b=0.01 to 1.0, c=0.01 to 1.0, d=0.01 to 1, and $0.001 < e \leq 0.10$; where e is 0.015-0.03, said catalyst produced by the process comprising:

i) admixing compounds of elements Mo, V, Te, and Nb, in a solvent comprising water;
ii) heating said first mixture in a first closed vessel at a temperature of from 100° C. to 200° C. for from 24 hours to 240 hours;
iii) recovering first insoluble material from steps ii) and iii);
iv) subjecting said first recovered insoluble material to calcining to produce the calcined product;
v) then, impregnating said calcined product with of a Pd compound free of halogens to form second mixture containing elements Mo, V, Te, Nb, and Pd;
vi) subjecting said second mixture to a drying step at a temperature of from 50° C. to 150° C., (or from 110° C. to 140° C., or from 120° C. to 130° C.), for from 1 hour to 48 hours; and
vii) recovering second insoluble material to obtain a catalyst.

Provided is a mixed metal oxide catalyst of the formula Mo—V—Nb—Te—Pd—O, in the respective relative atomic proportions of a, b, c, d, and e wherein when a=1, b=0.01 to 1.0, c=0.01 to 1.0, d=0.01 to 1, and $0.001 < e \leq 10$; where e is 0.015-0.03, said catalyst produced by the process comprising:

viii) admixing compounds of elements Mo, V, Te, and Nb, in a solvent comprising water;
ix) heating said first mixture in a first closed vessel at a temperature of from 100° C. to 200° C. for from 24 hours to 240 hours;
x) recovering first insoluble material from steps ii) and iii);
xi) subjecting said first recovered insoluble material to calcining to produce the calcined product;
xii) then, impregnating said calcined product with of a Pd compound free of halogens to form second mixture containing elements Mo, V, Te, Nb, and Pd;
xiii) subjecting said second mixture to a drying step at a temperature of from 50° C. to 150° C., (or from 110° C. to 140° C., or from 120° C. to 130° C.), for from 1 hour to 48 hours; and
xiv) recovering second insoluble material to obtain a catalyst.

Other than in the operating examples or where otherwise indicated, all numbers or expressions referring to quantities of ingredients, reaction conditions, etc. used in the specification and claims are to be understood as modified in all instances by the term "about." Accordingly, unless indicated to the contrary, the numerical parameters set forth in the following specification and attached claims are approximations that can vary depending upon the properties that the present disclosure desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

All compositional ranges expressed herein are limited in total to and do not exceed 100 percent (volume percent or weight percent) in practice. Where multiple components can be present in a composition, the sum of the maximum amounts of each component can exceed 100 percent, with the understanding that, and as those skilled in the art readily understand, that the amounts of the components actually used will conform to the maximum of 100 percent.

Disclosed is a mixed metal oxide catalyst for the oxidative dehydrogenation of ethane into ethylene, said catalyst having the empirical formula $Mo_aV_bTe_cNb_dPd_eO_f$, wherein a, b, c, d, e and f are the relative atomic amounts of the elements Mo, V, Te, Nb, Pd and O, respectively, and when a=1, b=0.01 to 1.0, c=0.01 to 1.0, d=0.01 to 1, $0.001 < e \leq 0.10$ and f is dependent on the oxidation state of the other elements. The addition of small amounts of Pd into the catalyst provides an increase in activity while maintaining high selectivity for ethylene when compared to a catalyst comprised solely of Mo, V, Te, Nb, and O. The increase in activity without comprising selectivity is dependent upon the method of incorporation of Pd and the nature of the Pd compound used for incorporation into the catalyst.

The process for admixing multiple compounds in a solvent such as water for the purpose of constructing a catalyst for oxidative dehydrogenation of paraffins is well known in the art. The compounds are mixed using amounts of each compound that will result in a catalyst containing the desired relative atomic amounts of each compound. For the purposes of the present disclosure, aqueous solutions containing compounds with the individual elements represented in the catalyst are one embodiment of source material for each element.

The efficiency of the catalyst disclosed herein is dependent upon the relative atomic amounts of each element, indicated by the subscripts a, b, c, d, e, f, in the formula for the catalyst, $Mo_aV_bTe_cNb_dPd_eO_f$. For all formulations the relative atomic amount of molybdenum, as represented by subscript a, is 1. The value of f, the relative atomic amount of oxygen in the catalyst, in all instances, depends on the oxidation state of all other elements present in the catalyst. In one embodiment b=0.01 to 1.0, c=0.01 to 1.0, d=0.01 to 1.0, and $0.01 < e \leq 0.10$.

In one embodiment, the relative atomic amount of the element vanadium, indicated by subscript b, equals from 0.1 to 0.5. In another embodiment, b equals from 0.2 to 0.4. In a further embodiment b equals from 0.25 to 0.35.

In an embodiment, the relative atomic amount of the element tellurium, indicated by subscript c, equals from 0.05 to 0.4. In another embodiment, c equals from 0.08 to 0.3. In a further embodiment, c equals from 0.10 to 0.25.

In an embodiment, the relative atomic amount of the element niobium, indicated by subscript d, equals from 0.05 to 0.4. In another embodiment, c equals from 0.08 to 0.3. In a further embodiment, c equals from 0.10 to 0.25.

Hydrothermal synthesis for preparation of mixed metal oxide catalysts is known in the art, its advantages over conventional preparation methods such as solid-state reaction and dry-up are covered in Watanabe, et al., "New Synthesis Route For Mo—V—Nb—Te Mixed Metal Oxides For Propane Ammoxidation", Applied Catalysis A: General, 194-195, pp. 479-485 (2000).

One embodiment described herein comprises a hydrothermal synthesis step for preparation of the catalyst prior to addition of the Pd compound. Compounds containing elements Mo, V, Nb, and Te and a solvent are mixed to form a first mixture. The first mixture is then heated in a pressurized vessel for from 6 to 240 hours. In one embodiment, the solvent used for hydrothermal synthesis of the first mixture is water. Any water suitable for use in chemical syntheses can be utilized, and includes, without limitation, distilled water, de-ionized, and mineral water. The amount of solvent used is not critical.

Preparation of the mixture is not limited to addition of all compounds of Mo, V, Nb, and Te at the same time prior to heat treatment in a first closed vessel. For example, the Mo and Te compounds may be added first, followed by the V compound and eventually the Nb compound. For a further example, the process may be reversed in that the Te and Nb compounds are combined followed by addition of a mixture of the Mo and V compounds. Other sequences of addition would be apparent to a person skilled in the art. Sequence and timing of addition is not limited by these examples.

In one embodiment, the first mixture is heated at a temperature of from 100° C. to 200° C. In another embodiment, the first mixture is heated at a temperature from 130° C. to 190° C. In a further embodiment, the first mixture is heated at a temperature from 160° C. to 185° C.

Following hydrothermal synthesis of the first four components of the catalyst the first insoluble material is recovered from the pressurized vessel. At this point, the first insoluble material may be dried prior to calcining in order to remove any residual solvent. Any method known in the art may be used for optional drying of the first insoluble material, including, but not limited to, air drying, vacuum drying, freeze drying, and oven drying.

Methods for calcination are well known in the art. Herein, the calcining of the first insoluble material is conducted under an inert atmosphere. In one embodiment, the calcination vessel is a quartz tube. The inert atmosphere may include any material that does not interact or react with the first insoluble material. Examples include, without limitation, nitrogen, argon, xenon, helium or mixtures thereof. One embodiment disclosed herein comprises an inert atmosphere comprising gaseous nitrogen.

Calcination methods for preparation of mixed metal oxide catalysts vary in the art. Variables include the time, temperature range, the speed of heating, use of multiple temperature stages, and the use of an oxidizing or inert atmosphere. For the present disclosure the speed of heating is not critical and may range from between 0.1° C./minute to around 10° C./minute. Also, the inert gas may be present statically or may be passed over the catalyst at flow rates where the loss of catalyst is minimized, i.e. carryover out of bed.

In an embodiment, the said first recovered insoluble material is calcined by ramping temperature from at or about room temperature to at or about 600° C. over a period of 4 to 7 hours, followed by holding at or about 600° C. for from 1 hour to 4 hours.

In an embodiment, the time for the calcining ranges from 1 hour to 24 hours. In another embodiment the time for the calcining ranges from 3 hours to 15 hours. In one embodiment the time for the calcining ranges from 4 hours to 12 hours.

In an embodiment, the calcining takes place in an inert atmosphere at a temperature from 500° C. to 700° C. In another embodiment the calcining takes place in an inert atmosphere at a temperature from 550° C. to 650° C. In another embodiment the calcining takes place in an inert atmosphere at a temperature of from 580° C. to 620° C.

Following the calcining, the calcining product is impregnated with a Pd component free of halogens to form a second mixture. For the present disclosure the addition of a Pd component to the catalyst is effective in increasing the activity of the catalyst, without significantly decreasing the selectivity, depending on the method for addition and the nature of the Pd compound used. The addition of the Pd compound is performed following the calcining of the first insoluble material containing the four components Mo, V, Te, and Nb.

In an embodiment, the Pd compound, in the form of an aqueous solution, is added dropwise to the calcining product until saturation. In another embodiment, the Pd component and the calcining product are mixed in an aqueous solution to form a slurry. In an embodiment the aqueous solution is water. Any water suitable for use in chemical syntheses can be utilized, and includes, without limitation, distilled water and de-ionized water. The amount of solvent used is not critical.

The amount of Pd component added, either in dropwise fashion or in a slurry, will correspond roughly with 0.044 mmol Pd/$g_{ODH\ catalyst}$ to yield a final relative atomic amount of Pd, represented by the subscript e in the formula $Mo_aV_bTe_cNb_dPd_eO_f$, between 0.001 and 0.1.

The nature of the Pd compound used must be free of halogens. A catalyst produced as described herein where the Pd component used is $PdCl_2$, fails to show any activity at all. In one embodiment the Pd component used is tetra-amine Pd nitrate, chemically represented by the formula $[Pd(NH_3)_4](NO_3)_2$. In another embodiment the Pd component used is palladium (II) hydrogen carbonate, chemically represented by the formula $Pd(HCO_3)_2$. In another embodiment the Pd component used is palladium (II) acetate, chemically represented by the formula $Pd(CH_3COO)_2$ Following incorporation of the Pd component, a second insoluble material is dried and recovered for use as a catalyst. Drying steps are commonly used in the art. In an embodiment the temperature for drying the second insoluble material ranges from 50° C. to 150° C. In another embodiment the temperature for drying the second insoluble material ranges from 110° C. to 140° C. In an embodiment the temperature for drying the second insoluble material ranges from 120° C. to 130° C.

In an embodiment, the time for drying the second insoluble material ranges from 1 hour to 48 hours. In another embodiment the time for drying the second insoluble material is from 8 hours to 36 hours. In another embodiment the time for drying the second insoluble material is from 12 hours to 24 hours.

The dried second insoluble material is recovered and can be used directly as a catalyst for ODH, using conditions where the only atmospheric components exposed to the catalyst are oxygen and ethane. The ratios of oxygen and ethane and the temperature used for the ODH process are such that the upper explosive limit is not triggered. The ability to perform ODH using this catalyst whereby there is no dilution of the reactants with nitrogen or other inert gas or water confers a commercial advantage as costly downstream processes for the removal of excess oxygen or any unwanted byproducts are not required or are limited in nature.

EXAMPLES

Comparative Example 1 (No Pd Component)

a. 2.65 g of ammonium heptamolybdate (tetrahydrate) and 0.575 g of telluric acid were dissolved in 19.5 g of distilled water at 80° C. and the pH adjusted to 7.5 using a 25% aqueous solution of ammonium hydroxide. The water was evaporated by stirring at 80° C., and the solid precipitate dried at 90° C. 3.0 g of the precipitate was suspended in water (21.3 g) at 80° C. and 0.9 g of vanadyl sulfate and 1.039 g of niobium oxalate were added. The mixture was stirred for 10 min and then transferred to an autoclave with a Teflon® (tetrafluoroethylene) lining. Air in the autoclave was substituted with argon, the autoclave was pressurized and heated to 175° C. for 60 hours. The solid formed was filtered, washed with distilled water and dried at 80° C. to produce an active catalyst phase that was calcined at 600° C. (2 h) in a flow of argon. The temperature for calcination was ramped from room temperature to 600° C. at 1.67° C./min. The resulting powder was pressed and the required mesh size particles were collected. The resulting catalyst comprised an atomic element ratio (oxygen not included) of $Mo_{1.0}V_{0.31}Te_{0.17}Nb_{0.16}$.—calculated by molar ratio stoichiometry of reagents.

Comparative Example 2 (Impregnation with $PdCl_2$)

b. The catalyst was prepared according to Comparative Example 1 with the exception that after calcining the sample at 600° C., the catalyst was ground in a mortar with a small amount of water (about 5 ml per gram of the catalyst) for 20 min. The suspension of the catalyst in water was transferred into a glass beaker (volume 50 ml) and then a solution containing 0.1 mmol of $PdCl_2$ in 10 ml of water was added to the suspension. The beaker content was stirred by a magnetic stirrer with a low rate for 2 h. The beaker was placed in a water bath at a temperature of 80° C. and the content was stirred until the liquid in the beaker was fully removed. The beaker with the catalyst was transferred into a drying box and was dried overnight at 120° C. The catalyst obtained was ground in a mortar and pressed into tablets that were crashed into particles 0.8-1.0 mm. The resulting catalyst comprised an atomic element ratio (oxygen not included) of $Mo_{1.0}V_{0.31}Te_{0.17}Nb_{0.16}Pd_{0.02}$.—calculated by molar ratio stoichiometry of reagents.

Comparative Example 3 (Direct Pd Incorporation)

c. 2.65 g of ammonium heptamolybdate (tetrahydrate) and 0.575 g of telluric acid were dissolved in 19.5 g of distilled water at 80° C. and the pH adjusted to 7.5 with a 25% aqueous solution of ammonium hydroxide. Water was evaporated by stirring at 80° C. The solid precipitate was dried at 90° C. 3.0 g of the precipitate was suspended in water (21.3 g) at 80° C. and 0.9 g of vanadyl sulfate and 1.039 g of niobium oxalate were added together with palladium in the form of $[Pd(NH_3)_4](NO_3)_2]$ in amounts to produce an atomic element ratio (oxygen not included) of $Mo_{1.0}V_{0.31}Te_{0.17}Nb_{0.16}Pd_{0.02}$. The catalyst was calcined at 600° C. (2 h) in a flow of argon, where the temperature was ramped from room temperature to 600° C. at 1.67° C./min. The powder was pressed and the required mesh size particles were collected.

Example 1 (Pd Nitrate Incorporation)

d. The catalyst was prepared according to Comparative Example 1 with the exception that after calcining the sample at 600° C., the catalyst was ground in a mortar with a small amount of water (about 5 ml per gram of the catalyst) for 20 min. The suspension of the catalyst in water was transferred into a glass beaker (volume 50 ml) and then a solution containing 0.1 mmol of $[Pd(NH_3)_4](NO_3)_2]$ in 10 ml of water was added to the suspension. The beaker content was stirred by a magnetic stirrer at a low rate for 2 h. The beaker was placed in a water bath at a temperature of 80° C. and the content was stirred until the liquid in the beaker had evaporated completely. The beaker with the catalyst was transferred into a drying box and was dried overnight at 120° C. The resulting catalyst was ground in a mortar and pressed into tablets that were crushed into particles 0.8-1.0 mm. The resulting catalyst comprised an atomic element ratio (oxygen not included) of $Mo_{1.0}V_{0.31}Te_{0.17}Nb_{0.16}Pd_{0.02}$.

Example 2 (Pd Carbonate Incorporation)

e. The catalyst was prepared according to Example 1 with the exception that after calcining the sample at 600° C., the catalyst was treated with an aqueous solution of $Pd(HCO_3)_2$ to introduce the amount of palladium corresponding to a final atomic element ratio (oxygen not included) of $Mo_{1.0}V_{0.31}Te_{0.17}Nb_{0.16}Pd_{0.02}$.

Example 3 (Pd Acetate Incorporation)

f. The catalyst was prepared according to Example 1 with the exception that after calcining the sample at 600° C., the catalyst was treated with an aqueous solution of $Pd(CH_3COO)_2$ to introduce the amount of palladium corresponding to a final atomic element ration (oxygen not included) of $Mo_{1.0}V_{0.31}Te_{0.17}Nb_{0.16}Pd_{0.02}$.

ODH Testing Conditions g. All catalysts were tested for ability to catalyze oxidative dehydrogenation of ethane using a gas mixture $O_2/C_2H_6$ with an $O_2$ content of 25% (outside the explosive limit). The mixture was fed into a plug-flow reactor with a gas hourly space velocity of 4500 $h^{-1}$ at a pressure of 1 atm, and a temperature that ranged from 320-440° C. (or for example at 420° C.). The amount of catalyst loading ranged from 0.13-1.3 g; fraction 0.25-0.5 mm, a flow type reactor with a stationary catalyst bed was used. The catalyst was heated to 360° C. in the reaction mixture and the catalytic activity was measured at 420° C. The data are presented in Table 1.

TABLE 1

Summary of results

| Example | Ethane conversion, % | Oxygen conversion, % | Space-time yield of ethylene (Productivity). mmol/h per g of catalyst | Ethylene Selectivity % |
|---|---|---|---|---|
| 1 (Comparative) | 33 | 56 | 60 | 97.5 |
| 2 (Comparative) | 6 | 17 | — | 96 |
| 3 (Comparative) | 31 | 53 | 55 | 97 |
| 1 | 49 | 83 | 94 | 98 |
| 2 | 48 | 81 | 91 | 98 |
| 3 | 46 | 80 | 88 | 98 |

What is claimed is:

1. A process for preparing an oxidative dehydrogenation catalyst comprising a mixed metal oxide having the empirical formula $$Mo_a V_b Te_c Nb_d Pd_e O_f$$

wherein
- a, b, c, d, e and f are the relative atomic amounts of the elements Mo, V, Te, Nb, Pd, and O, respectively; and a is 1, b is from 0.01 to 1.0, c is from 0.01 to 1.0, d is from 0.01 to 0.1.0, e is from 0.0001 to less than 0.10, and f is dependent on the oxidation state of the other elements;

the process comprising:
- admixing compounds of elements Mo, V, Te, and Nb, in a solvent comprising water to produce a first mixture;
- heating the first mixture in a first pressurized vessel at a temperature of from 100° C. to 200° C.;
- recovering a first insoluble material from the first pressurized vessel;
- subjecting the first recovered insoluble material to a calcining at a temperature of from 500° C. to 700° C. under an inert atmosphere to produce a calcined product;
- contacting the calcined product with an aqueous solution comprising a Pd compound to form second mixture, wherein the aqueous solution comprising the Pd compound is prepared from a Pd compound chosen from [Pd(NH$_3$)$_4$](NO$_3$)$_2$, Pd(HCO$_3$)$_2$, Pd(CH$_3$COO)$_2$ an analogous Pd containing salt, or a combination thereof;
- subjecting the second mixture to drying to provide a dried product; and
- recovering a second insoluble material from the dried product to provide the catalyst, and wherein the process excludes calcination after the impregnation of Pd.

2. The process of claim 1, wherein the first mixture in the first pressurized vessel is heated for from 6 hours to 240 hours.

3. The process of claim 1, wherein the first recovered insoluble material is calcined for from 1 hour to 8 hours.

4. The process of claim 1, wherein the second mixture is dried at a temperature of from 50° C. to 150° C.

5. The process of claim 1, wherein the second mixture is dried for from 1 hour to 48 hours.

6. The process of claim 1, wherein heating of the first mixture in the first pressurized vessel is done at a temperature of from 160° C. to 185° C.

7. The process of claim 1, wherein the drying temperature is from 120° C. to 130° C.

8. The process of claim 1, wherein the inert atmosphere comprises gaseous nitrogen.

9. The process of claim 1, wherein the first recovered insoluble material is calcined by ramping the temperature from at or about room temperature to at or about 600° C. over a period of 4 to 7 hours, followed by holding at or about 600° C. for from 1 hour to 4 hours.

10. The process of claim 1, wherein b is from 0.1 to 0.5.

11. The process of claim 1, wherein b is from 0.2 to 0.4.

12. The process of claim 1, wherein c is from 0.05 to 0.4.

13. The process of claim 1, wherein c is from 0.08 to 0.3.

14. The process of claim 1, wherein d is from 0.05 to 0.4.

15. The process of claim 1, wherein d is from 0.08 to 0.3.

16. The process of claim 1, wherein d is from 0.10 to 0.25.

17. The process of claim 1, wherein e is from 0.005 to 0.10.

18. The process of claim 1, wherein e is from 0.01 to 0.05.

19. The process of claim 1, wherein e is from 0.015 to 0.03.

* * * * *

UNITED STATES PATENT AND TRADEMARK OFFICE
CERTIFICATE OF CORRECTION

PATENT NO. : 11,691,130 B2
APPLICATION NO. : 16/747131
DATED : July 4, 2023
INVENTOR(S) : Vasily Simanzhenkov et al.

It is certified that error appears in the above-identified patent and that said Letters Patent is hereby corrected as shown below:

On the Title Page

Column 1, Line 1, (73) Assignee, please replace "S.A." with -- S.A., Fribourg (CH) --.

Signed and Sealed this
Twelfth Day of December, 2023

Katherine Kelly Vidal
*Director of the United States Patent and Trademark Office*